(12) United States Patent
Tanaka et al.

(10) Patent No.: US 7,223,859 B2
(45) Date of Patent: May 29, 2007

(54) METHOD FOR PRODUCING (R)-3-[4-(TRIFLUOROMETHYL) PHENYLAMINO]-PENTANOIC ACID AMIDE DERIVATIVE

(75) Inventors: Tatsuyoshi Tanaka, Takasago (JP); Masanobu Sugawara, Takasago (JP); Hirofumi Maeda, Takasago (JP); Akira Nishiyama, Takasago (JP); Yoshihiko Yasohara, Takasago (JP); Nobuo Nagashima, Takasago (JP)

(73) Assignee: Pfizer Inc., New York, NY (US)

( * ) Notice: Subject to any disclaimer, the term of this patent is extended or adjusted under 35 U.S.C. 154(b) by 511 days.

(21) Appl. No.: 10/801,141

(22) Filed: Mar. 16, 2004

(65) Prior Publication Data

US 2004/0199005 A1    Oct. 7, 2004

Related U.S. Application Data

(60) Provisional application No. 60/462,687, filed on Apr. 15, 2003.

(30) Foreign Application Priority Data

Mar. 17, 2003   (JP) ............................. 2003-072358
Apr. 1, 2003    (JP) ............................. 2003-098452

(51) Int. Cl.
*C07D 205/02*    (2006.01)
*C07C 233/00*    (2006.01)

(52) U.S. Cl. ...................................... 540/200; 564/194

(58) Field of Classification Search ................ 540/200; 564/194

See application file for complete search history.

(56) References Cited

U.S. PATENT DOCUMENTS 3,773,620 A * 11/1973 Kimura et al. .............. 435/144
5,227,538 A *  7/1993 Buchwald et al. .......... 568/814
6,706,881 B2 * 3/2004 Damon et al. .............. 546/159

FOREIGN PATENT DOCUMENTS

WO    WO 02/088069 A2    11/2002
WO    WO 02/088085 A2    11/2002
WO    WO 02088085 A2 *  11/2002

* cited by examiner

*Primary Examiner*—Kamal A. Saeed
(74) *Attorney, Agent, or Firm*—Gregg C. Benson; Lisa A. Samuels

(57) ABSTRACT

The present invention provides a method for easily producing an (R)-3-[4-(trifluoromethyl)phenylamino]-pentanoic acid amide derivative useful for an intermediate for pharmaceutical products, particularly an inhibitor of a cholesteryl ester transfer protein (CETP) from easily available raw materials. In the present invention, (S)-N-[4-(trifluoromethyl)phenyl]-3-hydroxypentanoic acid amide prepared from easily available raw materials leads a production of (R)-4-ethyl-1-[4-(trifluoromethyl)phenyl]-2-azetidinone to give (R)-3-[4-(trifluoromethyl)phenylamino]-pentanoic acid amide. Furthermore, (R)-4-ethyl-1-[4-(trifluoromethyl)phenyl]-2-azetidinone is reacted with a carbamic acid ester to give an (R)-3-[4-(trifluoromethyl)phenylamino]-pentanoic acid amide derivative.

4 Claims, No Drawings

METHOD FOR PRODUCING (R)-3-[4-(TRIFLUOROMETHYL) PHENYLAMINO]-PENTANOIC ACID AMIDE DERIVATIVE

This application claims priority to No. JP 2003-072358 filed on 17 Mar. 2003, No. JP 2003-098452 filed 1 Apr. 2003, and U.S. Provisional Application No. 60/462,687 filed 15 Apr. 2003, the contents of which are incorporated herein by reference in their entirety.

TECHNICAL FIELD

The invention relates to a method for producing an (R)-3-[4-(trifluoromethyl)phenylamino]-pentanoic acid amide derivative useful for an intermediate for pharmaceutical products, particularly an inhibitor of a cholesteryl ester transfer protein (CETP).

BACKGROUND ART

Conventionally, the following methods have been known as methods producing an (R)-3-[4-(trifluoromethyl)phenylamino]-pentanoic acid amide derivative.

That is, an amino group of (R)-2-amino-1-butanol is protected by a tert-butoxycarbonyl group, and then mesylation and/or cyanation of a hydroxyl group and protection release of an amino protecting group are successively carried out to produce (R)-3-aminopentanenitrile. Thereafter, the product is coupled with 4-(trifluoromethyl)chlorobenzene using a catalyst produced from palladium acetate and 2-dicyclohexylphosphino-2'-(N,N-dimethylamino)-1,1'-biphenyl to produce (R)-3-[4-(trifluoromethyl)phenylamino]-pentanenitrile. Then, this product is hydrated with concentrated sulfuric acid to produce (R)-3-[4-(trifluoromethyl)phenylamino]-pentanoic acid amide. Furthermore, the (R)-3-[4-(trifluoromethyl)phenylamino]-pentanoic acid amide is reacted with a chlorocarbonic acid ester in the presence of a base to be converted into an (R)-3-[4-(trifluoromethyl)phenylamino]-pentanoic acid amide derivative (WO 02/088069, WO 02/088085).

However, the method comprises a large number of steps, using a highly toxic sodium prussiate and even using very expensive palladium catalyst and phosphine ligand, and therefore, the method cannot necessarily be said to be industrially advantageous.

SUMMARY OF THE INVENTION

Taking the above-mentioned situation into consideration, the purpose of the invention is to provide a method for easily producing an (R)-3-[4-(trifluoromethyl)phenylamino]-pentanoic acid amide derivative useful for an intermediate for pharmaceutical products, particularly an inhibitor of a cholesteryl ester transfer protein (CETP), from economical and easily available raw materials.

Based on the results of enthusiastic investigations for satisfying the above-mentioned purpose, the present inventors have developed a method for easily producing an (R)-3-[4-(trifluoromethyl)phenylamino]-pentanoic acid amide derivative from economical and easily available raw materials.

The present invention, therefore, relates to a method for producing an (R)-3-[4-(trifluoromethyl)phenylamino]-pentanoic acid amide derivative defined by the following formula (8):

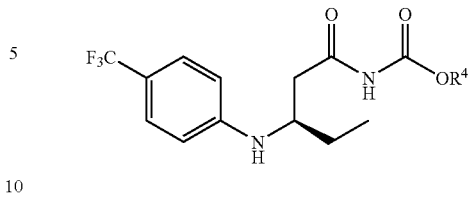

(8)

in the formula, $R^4$ denotes a $C_{1-12}$ alkyl, a $C_{6-12}$ aryl or a $C_{7-12}$ aralkyl group:

which comprises reacting (R)-4-ethyl-1-[4-(trifluoromethyl)phenyl]-2-azetidinone defined by the following formula (2):

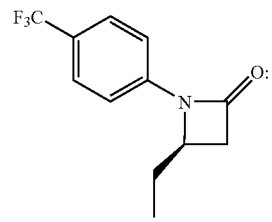

(2)

with a carbamic acid ester defined by the following formula (9):

$$NH_2COOR^4 \quad (9)$$

in the formula, $R^4$ denotes the same described above: in the presence of a base.

The invention relates to a method for producing (R)-3-[4-(trifluoromethyl)phenylamino]-pentanoic acid amide defined by the following formula (3):

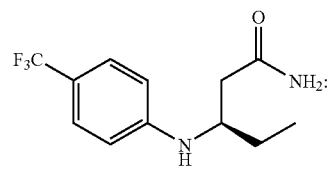

(3)

which comprises
i) amidation of (R)-4-ethyl-1-[4-(trifluoromethyl)phenyl]-2-azetidinone defined by the following formula (2):

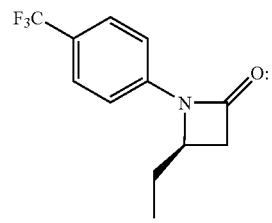

(2)

or
ii) amidation of an (R)-3-[4-(trifluoromethyl)phenylamino]-pentanoic acid derivative defined by the following formula (5):

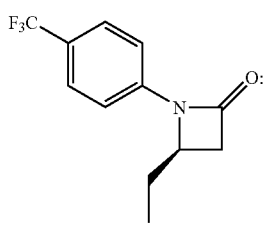

(5)

in the formula, $R^2$ denotes hydrogen atom or a $C_{1-5}$ alkyl group: obtained by hydrolysis or alcoholysis of the (R)-4-ethyl-1-[4-(trifluoromethyl)phenyl]-2-azetidinone defined by said formula (2).

The invention relates to a method for producing (R)-4-ethyl-1-[4-(trifluoromethyl)phenyl]-2-azetidinone defined by the following formula (2):

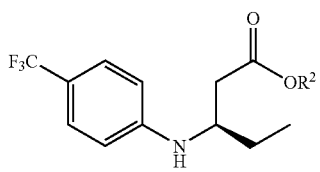

(2)

which comprises

I) cyclization of (S)-N-[4-(trifluoromethyl)phenyl]-3-hydroxypentanoic acid amide defined by the following formula (1):

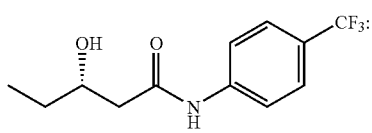

(1)

with a dehydration condensing agent, or

II) a production of an (S)-N-[4-(trifluoromethyl)phenyl]-3-sulfonyloxypentanoic acid amide derivative defined by the following formula (4):

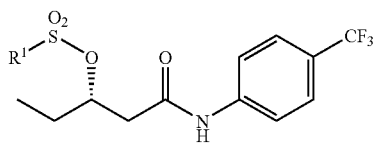

(4)

in the formula, $R^1$ denotes a $C_{1-12}$ alkyl group optionally having a substituent or a $C_{6-12}$ aryl group optionally having a substituent: by sulfonylation of the (S)-N-[4-(trifluoromethyl)phenyl]-3-hydroxypentanoic acid amide defined by said formula (1), and successive treatment with a base.

The invention relates to (S)-N-[4-(trifluoromethyl)phenyl]-3-hydroxypentanoic acid amide defined by the following formula (1):

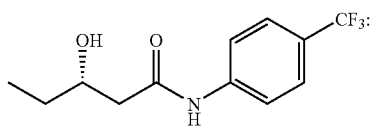

(1)

(R)-4-ethyl-1-[4-(trifluoromethyl)phenyl]-2-azetidinone defined by the following formula (2):

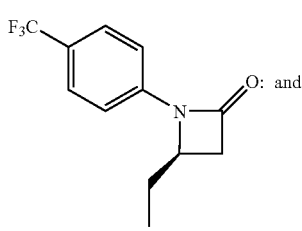

(2)

and an (S)-N-[4-(trifluoromethyl)phenyl]-3-sulfonyloxypentanoic acid amide derivative defined by the following formula (4):

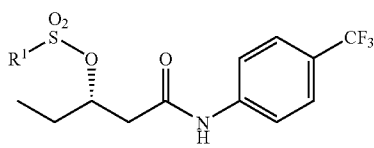

(4)

in the formula, $R^1$ denotes a $C_{1-12}$ alkyl group optionally having a substituent or a $C_{6-12}$ aryl group optionally having a substituent.

The invention relates to a method for isolating and purifying (R)-4-ethyl-1-[4-(trifluoromethyl)phenyl]-2-azetidinone defined by the following formula (2):

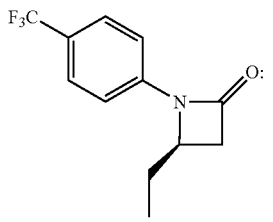

(2)

which comprises removing a contaminating (S)-4-ethyl-1-[4-(trifluoromethyl)phenyl]-2-azetidinone by crystallization from a hydrocarbon solvent to obtain the (R)-4-ethyl-1-[4-(trifluoromethyl)phenyl]-2-azetidinone defined by said formula (2) as a crystal with improved optical purity.

The invention relates to a method for isolating and purifying an (S)-N-[4-(trifluoromethyl)phenyl]-3-sulfonyloxypentanoic acid amide derivative defined by the following formula (4):

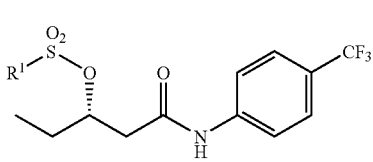

(4)

in the formula, $R^1$ denotes a $C_{1-12}$ alkyl group optionally having a substituent or a $C_{6-12}$ aryl group optionally having a substituent:

which comprises removing a contaminating (R)-N-[4-(trifluoromethyl)phenyl]-3-sulfonyloxypentanoic acid amide derivative by crystallization from an aromatic hydrocarbon solvent to obtain the (S)-N-[4-(trifluoromethyl)phenyl]-3-sulfonyloxypentanoic acid amide derivative defined by said formula (4) as a crystal with improved optical purity.

DETAILED DISCLOSURE OF THE INVENTION

The summary of the invention is expressed by the following scheme.

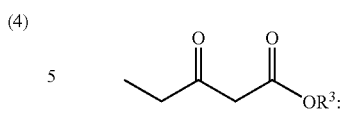

(6)

with 4-(trifluoromethyl)aniline is carried out to produce N-[4-(trifluoromethyl)phenyl]-3-oxopentanoic acid amide defined by the following formula (7):

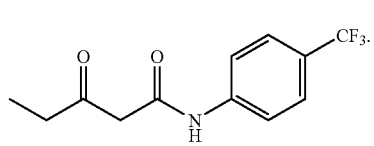

(7)

In the formula (6), $R^3$ denotes a $C_{1-5}$ alkyl group, more particularly methyl, ethyl, n-propyl, isopropyl, n-butyl, sec-butyl, tert-butyl, n-pentyl group, etc., and preferably methyl or ethyl group.

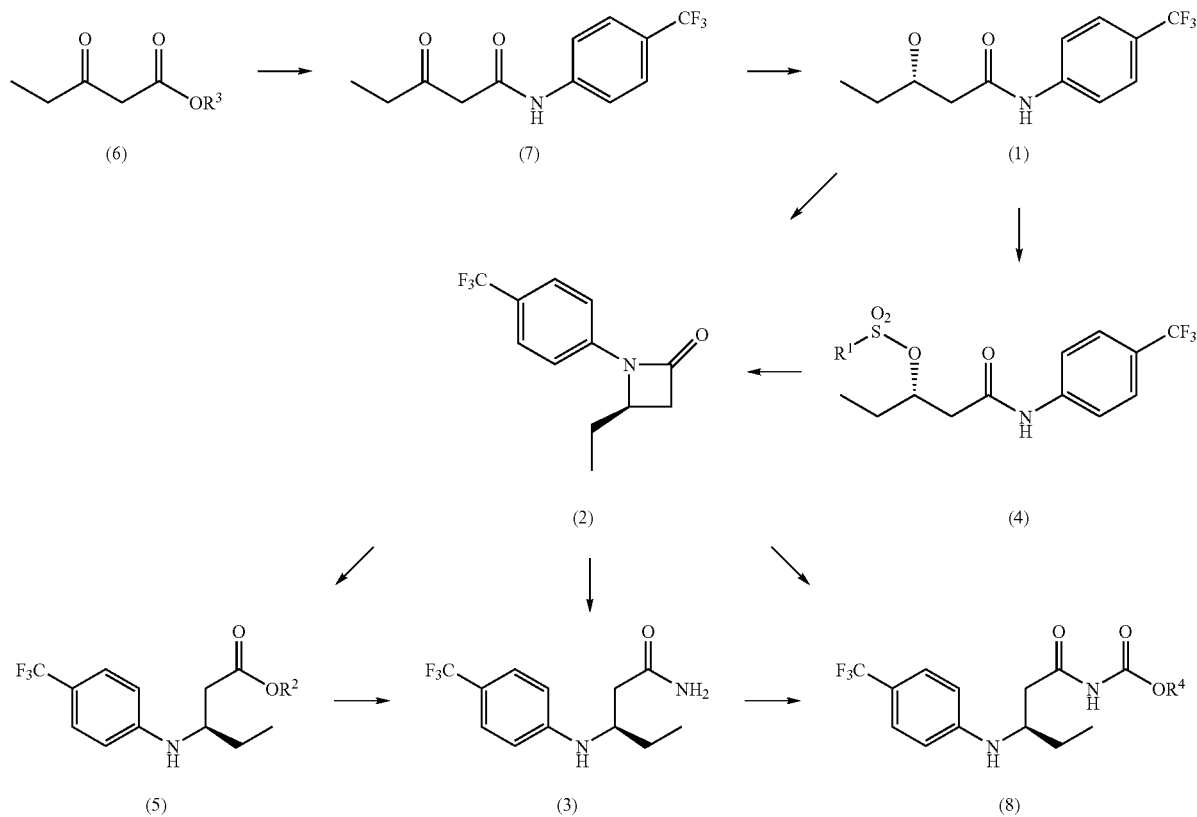

Hereinafter, the invention will be described in details along with the respective steps.

<Step From a Compound (6) to the Compound (7)>

In this step, a reaction of a 3-oxopentanoic acid ester derivative defined by the following formula (6):

The amount of the 4-(trifluoromethyl)aniline to be used is preferably 0.1 to 10 times, more preferably 0.5 to 2 times, by mole to that of the compound (6).

The reaction temperature is preferably 0 to 200° C., more preferably 50 to 150° C. in terms of shortening the reaction time and improving the yield.

The reaction may be carried out with no solvent or using a solvent for assuring the fluidity of the reaction mixture. In the case of using a solvent, for example, aromatic hydrocarbon solvents such as benzene, toluene, o-xylene, m-xylene, p-xylene, cumene and 1,3,5-mesitylene; alcohol solvents such as methanol, ethanol, isopropanol, n-butanol and ethylene glycol; ether solvents such as tetrahydrofuran, 1,4-dioxane, ethylene glycol dimethyl ether, diethylene glycol dimethyl ether and anisole; halogen solvents such as chloroform, carbon tetrachloride and chlorobenzene; and the like are mentioned. Preferred is an aromatic hydrocarbon solvent such as benzene, toluene, o-xylene, m-xylene, p-xylene, cumene, 1,3,5-mesitylene, etc. and further preferred is toluene, o-xylene, m-xylene, or p-xylene. They may be used alone or two or more of them may be used in combination. In the case of using two or more species, the mixingratio is not limited. The amount of the above-mentioned solvent to be used is preferably not more than 50 times, more preferably 1 to 10 times, by weight to that of the compound (6).

The addition method and addition order of a 3-oxopentanoic acid ester derivative, the 4-(trifluoromethyl)aniline and the reaction solvent in the reaction are not particularly limited.

In addition, in terms of improving the reaction yield, the reaction can be carried out with letting a by-produced alcohol out from the reaction system. Furthermore, for improving a flow efficiency of an alcohol, a method which comprises adding a reaction solvent continuously to let an alcohol out with a reaction solvent is preferred.

As the treatment after the reaction, a general treatment for obtaining a product from a reaction solution may be used. For example, heating under vacuum or the like treatment of the reaction solution on completion of the reaction may be carried out to remove the reaction solvent and obtain an aimed product. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

<Step From the Compound (7) to the Compound (1)>

In this step, (S)-N-[4-(trifluoromethyl)phenyl]-3-hydroxypentanoic acid amide defined by the following formula (1):

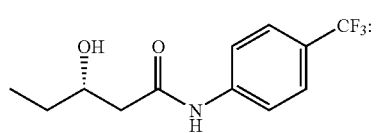

can be produced by asymmetric reduction of the N-[4-(trifluoromethyl)phenyl]-3-oxopentanoic acid amide defined by said formula (7).

Here, the (S)-N-[4-(trifluoromethyl)phenyl]-3-hydroxypentanoic acid amide defined by said formula (1) has not been reported in any document so far and thus is a novel compound and those containing S antipode in a slightly excess amount between both antipodes are all included in the invention.

The asymmetric reduction method in the step is not particularly limited if it is a method capable of selectively reducing the carbonyl group of the above-mentioned compound (7) into S antipode, and may include methods in which reduction is carried out by using a hydride reducing agent modified by an optically active compound; methods in which hydrogenation is carried out in the presence of an asymmetric transition metal catalyst; methods in which reduction is carried out in the presence of an asymmetric transition metal catalyst by a hydrogen transferring manner; methods in which reduction is carried out by using a microorganism or an enzyme derived from a microorganism; and the like methods.

More practically, the hydride reducing agent modified by an optically active compound may be a reducing agent produced from optically active tartaric acid and sodium borohydride; a reducing agent produced from an optically active oxazaborolidine derivative and borane; a reducing agent produced from an optically active ketoiminato type cobalt complex, sodium borohydride and tetrahydrofuran-2-methanol; a reducing agent produced from optically active 1,1'-bi-2-naphthol and lithium aluminum hydride; or the like.

In the case that hydrogenation is carried out in the presence of an asymmetric transition metal catalyst, as the asymmetric transition metal catalyst, ametal complex of a group VIII element in a periodic table such as ruthenium, rhodium, iridium, platinum, etc. is preferable and in terms of stability of a complex, availability and economical properties, a ruthenium complex is more preferable. As an asymmetric ligand in the metal complex, a phosphine ligand is preferable and as the phosphine ligand, a bidentate ligand is preferable. As preferable bidentate ligand is BINAP (2,2'-bisdiphenylphosphino-1,1'-binaphthyl); BINAP derivatives such as Tol-BINAP (2,2'-bis(di-p-tolylphosphino)-1,1'-binaphthyl); BDPP (2,4-bis(diphenylphosphino)pentane); DIOP (4,5-bis(diphenylphosphinomethyl)-2,2-dimethyl-1,3-dioxane); BPPFA (1-[1',2-bis(diphenylphosphino)ferrocenyl]ethylamine); CHIRAPHOS (2,3-bis(diphenylphosphino)butane); DEGPHOS [1-substituted-3,4-bis(diphenylphosphino)pyrrolidine]; DuPHOS (1,2-bis(2,5-substituted phosphorano)benzene); DIPAMP (1,2-bis[(o-methoxyphenyl)phenylphosphino]ethane); etc., a further preferable ligand is BINAP (2,2'-bisdiphenylphosphino-1,1'-binaphthyl), and in order to reduce a carbonyl group selectively into S antipode a carbonyl group, (S)-BINAP may be used. As the (S)-BINAP complex, ((S)-BINAP)RuBr$_2$, ((S)-BINAP)RuCl$_2$, [((S)-BINAP)RuCl$_2$]$_2$NEt$_3$, etc. is preferable. The amount of the asymmetric transition metal catalyst to be used is preferably not more than 0.1 time, more preferably 0.0001 to 0.05 times, by mole to that of the compound (7).

The hydrogen pressure in the step is preferably 1 to 100 kg/cm$^2$, more preferably 1 to 30 kg/cm$^2$.

The reaction solvent may include water; alcohol solvents such as methanol, ethanol and isopropanol; ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone andmethyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphonic acid triamide solvents such as hexamethyl phosphonic acid triamide; and the like, and they may be used alone or two or more species maybe used in combination. Preferable is water or an alcohol solvent such as methanol, ethanol, isopropanol, etc. and more preferable is a mixed solvent of the above alcohol solvent and water. Furthermore preferable is a mixed solvent of methanol and water. In the case of using the mixed solvent of an alcohol solvent and water, the mixing ratio of an alcohol solvent/water is optional and the ratio of an alcohol solvent/water is preferably 100/1 to 1/1, more preferably 20/1 to 4/1, by volume. The amount of the solvent to be used is preferably 50 times or less, more preferably 5 to 20 times, by weight to that of the compound (7).

The reaction temperature is preferably −20 to 100° C., more preferably 0 to 60° C. in terms of shortening the reaction time and improving the reduction selectivity and the yield.

The addition method and addition order of the N-[4-(trifluoromethyl)phenyl]-3-oxopentanoic acid amide defined by said formula (7), the asymmetric reducing agent, and the solvent in the reaction are not particularly limited.

As the treatment after the reaction, a general treatment for obtaining a product from a reaction solution may be used. For example, after the transition metal catalyst is removed from the reaction solution by vacuum filtration or pressure filtration on completion of the reaction, heating under vacuum or the like treatment may be carried out to remove the reaction solvent and obtain an aimed product. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

The step may be also carried out using an enzyme source having activity of stereoselectively reducing the N-[4-(trifluoromethyl)phenyl]-3-oxopentanoic acid amide defined by said formula (7).

The microorganism to be used as the enzyme source can be found by the following method. At first, a cell is collected by centrifugation from 5 ml of a culture solution of the microorganism, and then the cell is suspended in a 100 mM phosphate buffer solution (pH 6.5; 2.5 ml) containing N-[4-(trifluoromethyl)phenyl]-3-oxopentanoic acid amide 2.5 to 1.25 mg and glucose 125 mg. The resultant is shaken in a test tube at 30° C. for 2 to 3 days. The aimed reducing capability can be evaluated by extracting the reaction solution with ethyl acetate after the reaction and analyzing N-[4-(trifluoromethyl)phenyl]-3-hydroxypentanoic acid amide produced in the extracted solution by high performance liquid chromatography.

The microorganism to be used may be the one satisfying the above-mentioned screening of bacteria, actinomycetes, fungi, yeasts and fungi imperfecti. Preferably used is, among others, a microorganism selected from the group consisting of *Arthrobacter, Bacillus, Brevibactrium, Clostridium, Corynebacterium, Flavobacterium, Luteococcus, Microbacterium, Pseudomonas, Paenibacillus, Serratia, Nocardia, Rathayibacter, Rhodococcus, Candida* and *Cryptococcus*.

Specifically, for example, there may be mentioned *Arthrobacter paraffineus* ATCC21218, *Bacillus cereus* IFO3466, *Bacillus subtilis* IAM1193, *Bacillus amyloliquefaciens* IFO3022, *Bacillus licheniformis* IFO12195, *Brevibacterium iodinum* IFO3558, *Clostridium cylindrosporum* IFO13695, *Corynebacterium flavescens* JCM1317, *Corynebacterium xerosis* IFO12684, *Flavobacterium flavescens* JCM7456, *Luteococcus japonicus* IFO12422, *Microbacterium lacticum* JCM1397, *Pseudomonas stutzeri* IFO13596, *Pseudomonas fluorescens* IFO3081, *Paenibacillus amylolyticus* IFO13625, *Paenibacillus polymyxa* IFO3020, *Paenibacillus alvei* IFO3343, *Serratia marcescens* IFO3046, *Nocardia globerula* IFO13510, *Rathayibacter rathayi* JCM9307, *Rhodococcus erythropolis* IFO12320, *Candida guilliermondii* IFO0454, *Candida intermedia* IFO0761, *Candida molischiana* IFO10296, *Cryptococcus albidus* IFO0378, etc.

The microorganism can be obtained in general from preserved strains easily available or easy to be purchased. It is also obtained by isolation from nature. Furthermore, the microorganism may be mutated to obtain microbial strains having more advantageous property for the reaction.

The microorganism may be cultured by the following method. To use it, any nutrient source which the microorganism can utilize in general may be used. For example, a saccharide such as glucose, sucrose, maltose, etc.; an organic acid such as lactic acid, acetic acid, citric acid, propionic acid, etc.; an alcohol such as ethanol, glycerin, etc.; a hydrocarbon such as paraffin, etc.; a fat and an oil such as soybean oil, rape oil, etc.; a mixture of the above substances, or the like carbon source can be used. And a nitrogen source such as ammonium sulfate, ammoniumphosphate, urea, yeast extract, meat extract, peptone, corn steep liquor, etc. may be added. Furthermore, a nutrient source such as other inorganic salt, a vitamin, etc. may properly be added.

The microorganism can be cultured generally under ordinal conditions. For example, a culture may be carried out at pH 4.0 to 9.5 in a temperature range of 20° C. to 45° C. for 10 to 96 hours in an aerobic condition.

In the invention, as the enzyme source, a enzyme obtainable from a cultured product of the microorganism and/or from the microorganism may be used. Here, the word "cultured product" means a culture solution, a condensed culture solution, a microorganism cell or a product obtained by a treatment of the microorganism cell.

The product obtained by a treatment of the microorganism cell is not particularly limited but includes, for example, dried cells obtained by drying treatment with acetone or diphosphorus pentoxide or by drying with a desiccator or a fan; cells treated with a surfactant; cells treated with a lysis enzyme; immobilized cells; cell-free extracted products obtained by breaking a cell; etc. Furthermore, an enzyme which catalyzes an enantiomer-selective reduction reaction may be purified from the cultured product and used.

In the reduction reaction, N-[4-(trifluoromethyl)phenyl]-3-oxopentanoic acid amide, which is a substrate, may be added all at once in an initial stage of the reaction or may be added separately along with the proceeding of the reaction.

The temperature of the reaction is generally 10 to 60° C., preferably 20 to 40° C., and pH of the reaction is 2.5 to 9, preferably 5 to 9.

The concentration of the microorganism in the reaction solution may properly be determined depending on the capability of the microorganism for reducing the substrate. The concentration of the substrate in the reaction solution is preferably 0.01 to 50% (W/V), more preferably 0.1 to 30% (W/V) The reaction is generally carried out by shaking or ventilating and stirring. The reaction time may properly be determined depending on the substrate concentration, the microorganism concentration, and other reaction conditions. In general, it is preferable to set the respective conditions so as to complete the reaction in 2 to 168 hours.

In order to promote the reduction reaction, an energy source such as glucose or ethanol is preferably added at a ratio of 1 to 30% to the reaction solution since it leads to preferable consequence. Furthermore, a coenzyme such as a reducing type nicotinamide-adenine dinucleotide (NADH)

and a reducing type nicotinamide-adenine dinucleotide phosphoric acid (NADPH), which are generally required in reduction reaction carried out by a biological method may be added to promote the reaction. Practically, the coenzyme may be added directly to the reaction solution or a reaction system for producing NADH or NADPH may be added to the reaction solution together with an oxidizing type coenzyme. For example, a reaction system for reducing NAD to NADH at the time that a formic acid dehydrogenase mediates a production of carbon dioxide and water from formic acid and a reaction system for reducing NAD or NADP to NADH or NADPH, respectively, at the time that a glucose dehydrogenase mediates a production of gluconolactone from glucose may be used.

Moreover, addition of a surfactant such as Triton (produced by NACALAI TESQUE INC.), Span (produced by Kanto Kagaku), Tween (produced by NACALAI TESQUE INC.), etc. to the reaction solution is effective. Furthermore, for the purpose of avoiding inhibition of the reaction by a substrate and/or an alcohol, which is a product of the reduction reaction, a water-insoluble organic solvent such as ethyl acetate, butyl acetate, isopropyl ether, toluene, etc. may be added to the reaction solution. Also, for the purpose of increasing the solubility of a substrate, a water-soluble organic solvent such as methanol, ethanol, acetone, tetrahydrofuran, dimethyl sulfoxide, etc. may be added.

The optically active N-[4-(trifluoromethyl)phenyl]-3-hydroxypentanoic acid amide produced by the reduction reaction can be isolated by extracting the reaction solution as such or after removing a cell, etc., with a solvent such as ethyl acetate and/or toluene and successive removal of the solvent. Furthermore, if a purification by a silica gel column chromatography, recrystallization or the like is carried out, the aimed compound with high purity can be obtained.

<Step From the Compound (1) to the Compound (2)>

In this step, the (S)-N-[4-(trifluoromethyl)phenyl]-3-hydroxypentanoic acid amide defined by said formula (1) is cyclized by using a dehydration condensing agent to obtain (R)-4-ethyl-1-[4-(trifluoromethyl)phenyl]-2-azetidinone defined by the following formula (2):

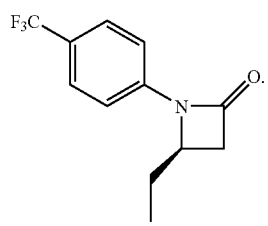

(2)

Here, the (R)-4-ethyl-1-[4-(trifluoromethyl)phenyl]-2-azetidinone defined by said formula (2) has not been reported in any document so far and thus is a novel compound and those containing R antipode in a slightly excess amount between both antipodes are all included in the invention.

The cyclization reaction can be carried out by using a dehydration condensing agent. The dehydration condensing agent may be a combination of agents of a phosphorane compound such as cyanomethylene-tributylphosphorane or cyanomethylene-trimethylphosphorane and/or an azo compound such as dimethyl azodicarboxylate, diethyl azodicarboxylate, diisopropyl azodicarboxylate or 1,1'-(azodicarbonyl)dipiperidine with a phosphine compound such as trimethylphosphine, tri-n-butylphosphine, tricyclohexylphosphine or triphenylphosphine, or the like agent. The dehydration condensing agent is preferably a combination of at least one azo compound selected from dimethyl azodicarboxylate, diethyl azodicarboxylate and diisopropyl azodicarboxylate, with at least one phosphine compound selected from tri-n-butylphosphine, tricyclohexylphosphine and triphenylphosphine.

The amount of the above-mentioned phosphorane compound to be used is preferably 1 to 10 times, more preferably 1 to 3 times, by mole to that of the above-mentioned compound (1). The amount of the above-mentioned azo compound to be used is preferably 1 to 5 times, more preferably 1 to 2 times, by mole to that of the above-mentioned compound (1). The amount of the phosphine compound to be used is preferably 1 to 5 times, more preferably 1 to 2 times, by mole to that of the above-mentioned compound (1).

The reaction solvent to be used may include ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphonic acid triamide solvents such as hexamethyl phosphonic acid triamide; and the like. Tetrahydrofuran, ethyl acetate, toluene and the like are preferable. They may be used alone or two or more of them may be used in combination. In the case of using two or more of them in combination, the mixing ratio is not limited. The amount of the above-mentioned reaction solvent to be used is preferably not more than 50 times, more preferably 5 to 20 times, by weight to that of the above-mentioned compound (1).

The reaction temperature is preferably −20 to 150° C., more preferably 0 to 100° C.

The addition method and addition order of the (S)-N-[4-(trifluoromethyl)phenyl]-3-hydroxypentanoic acid amide defined by said formula (1), the dehydration condensing agent and the solvent in the reaction are not particularly limited.

As the treatment after the reaction, a general treatment for obtaining a product from a reaction solution may be used. For example, heating under vacuum or the like treatment of the reaction solution on completion of the reaction may be carried out to remove the reaction solvent and obtain an aimed product. The aimed product obtained in such a manner has a sufficient purity to be subjected to the successive steps. Furthermore, the purity of the product may further be improved by a general purifying technique such as crystallization, fractional distillation, column chromatography, etc.

<Step From the Compound (1) to a Compound (4)>

In this step, the (S)-N-[4-(trifluoromethyl)phenyl]-3-hydroxypentanoic acid amide defined by said formula (1) is sulfonylated to obtain an (S)-N-[4-(trifluoromethyl)phenyl]-3-sulfonyloxypentanoic acid amide derivative defined by the following formula (4):

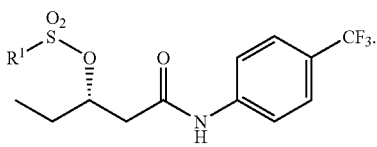

(4)

In the formula, $R^1$ denotes a $C_{1-12}$ alkyl group optionally having a substituent; a $C_{6-12}$ aryl group optionally having a substituent. $R^1$ may particularly include methyl, ethyl, chloromethyl, trifluoromethyl, phenyl, 4-methylphenyl, 4-chlorophenyl, 2-nitrophenyl, 3-nitrophenyl, 4-nitrophenyl groups and the like. $R^1$ is preferably methyl or 4-methylphenyl group.

The (S)-N-[4-(trifluoromethyl)phenyl]-3-sulfonyloxypentanoic acid amide derivative defined by said formula (4) has not been reported in any document so far and thus is a novel compound and those containing S antipode in a slightly excess amount between both antipodes are all included in the invention.

The step can be carried out by using a sulfonylation agent in the presence of a base. Here, the sulfonylation-agent may include sulfonyl halides, sulfonic acid anhydrides and the like. The sulfonyl halide may include methanesulfonyl chloride, ethanesulfonyl chloride, chlorometanesulfonyl chloride, benzenesulfonyl chloride, 4-methylbenzenesulfonyl chloride, 4-chlorobenzenesulfonyl chloride, 2-nitrobenzenesulfonyl chloride, 3-nitrobenzenesulfonyl chloride, 4-nitrobenzenesulfonyl chloride, and the like. The sulfonic acid anhydride may include trifluoromethanesulfonic acid anhydride and the like. Methanesulfonyl chloride or 4-methylbenzenesulfonylchlorideispreferable. The amount of the sulfonylation agent to be added is preferably 1 to 10 times, more preferably 1 to 3 times, by mole to that of the above-mentioned compound (1).

The above-mentioned base is not particularly limited but a tertiary amine is preferable. For example, triethylamine, tri-n-butylamine, N-methylmorpholine, N-methylpiperidine, diisopropylethylamine, pyridine, N,N-dimethylaminopyridine or the like can be used. More preferably, the base is triethylamine or pyridine. The amount of the base to be used is preferably 1 to 100 times, more preferably 1 to 3 times, by mole to that of the above-mentioned compound (1).

As the reaction solvent, the base may be used as the reaction solvent as it is or the following solvents may be used: ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphonic acid triamide solvents such as hexamethyl phosphonic acid triamide; and the like. Tetrahydrofuran, ethyl acetate or toluene is preferable. They may be used alone or two or more of them may be used in combination. In the case of two or more of them in combination, the mixing ratio is not particularly limited. The amount of the above-mentioned solvent to be used is preferably not more than 50 times, more preferably 5 to 20 times, by weight to that of the compound (1).

The reaction temperature is preferably −20 to 150° C., more preferably 0 to 100° C. in terms of shortening the reaction time and improving the yield.

The addition method and addition order of the (S)-N-[4-(trifluoromethyl)phenyl]-3-hydroxypentanoic acid amide defined by said formula (1), the sulfonylation agent, the base and the solvent are not particularly limited.

General treatment for obtaining a product from a reaction solution maybe carried out as the treatment after the reaction. For example, water and, optionally, an aqueous alkaline solution such as an aqueous sodium hydroxide solution or an aqueous sodium hydrogen carbonate solution or an aqueous acidic solution such as hydrochloric acid or sulfuric acid may be added to the reaction solution for neutralization on completion of the reaction, and then extraction may be carried out using a general extraction solvent, e.g. ethyl acetate, diethyl ether, methylene chloride, toluene, hexane, etc. The aimed substance can be obtained from the extracted solution by removing the reaction solvent and the extraction solvent by heating under vacuum or the like treatment. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

<Step of Isolating and Purifying the Compound (4)>

In this step, a contaminating (R)-N-[4-(trifluoromethyl)phenyl]-3-sulfonyloxypentanoic acid amide derivative is removed by crystallization from an aromatic hydrocarbon solvent to obtain the (S)-N-[4-(trifluoromethyl)phenyl]-3-sulfonyloxypentanoic acid amide derivative defined by said formula (4) as a crystal with improved optical purity. Here, $R^1$ is as described above and preferably methyl group.

The above-mentioned aromatic hydrocarbon solvent may include, for example, benzene, toluene, o-xylene, m-xylene, p-xylene, 1,3,5-mesitylene, cumene, etc. Preferred are toluene, o-xylene, m-xylene, p-xylene, etc., andmorepreferred is toluene. They may be used alone or two or more of them may be used in combination. In the case of using two or more species, the mixing ratio is not particularly limited.

The amount of the above-mentioned solvent to be used is preferably sufficient so as to keep the fluidity of the obtained product on completion of the crystallization of the compound (4) and it is preferably, for example, not more than 50 times, more preferably about 1 to 30 times, by weight to that of the compound (4).

In the present invention, the compound defined by said formula (4) may be crystallized by further using an auxiliary solvent in order to improve at least one among the yield, the treatment concentration and liquid property of the compound (4), and the physical property of the crystal to be obtained.

The auxiliary solvent is not particularly limited but may include, for example, alcohol solvents such as methanol, ethanol, isopropanol and n-butanol; ester solvents such as ethyl acetate, n-propyl acetate and tert-butyl acetate; ether solvents such as diethyl ether, tetrahydrofuran, 1,4-dioxane, methyl tert-butyl ether, dimethoxyethane and diisopropyl ether; ketone solvents such as acetone and methyl ethyl ketone; halogen solvents such as methylene chloride, chloroform and 1,1,1-trichloroethane; nitrile solvents such as acetonitrile and propionitrile; aliphatic hydrocarbon solvents such as pentane, hexane, heptane, cyclohexane, methylcyclohexane, octane and isooctane; and the like. The auxiliary solvents may be used alone or two or more of them may be used in combination. In the case of using two or more species, the mixing ratio is not limited. Preferred is an aliphatic hydrocarbon solvent such as pentane, hexane, heptane, cyclohexane, methylcyclohexane, octane, isooctane, etc., more preferred is hexane, heptane or methylcyclohexane. The preferred amount of the above-mentioned auxiliary solvent to be used may be determined by carrying out a simple experimentation. The preferred amount is the amount in which the ratio of the auxiliary solvent to the aromatic hydrocarbon solvent (the auxiliary solvent/the aromatic hydrocarbon solvent) by volume is not more than 10 on completion of crystallization. More preferred is the amount in which the ratio is not more than 1.

In this step, at the time of crystallization of the compound (4), crystallization methods such as cooling crystallization and concentration crystallization may be employed. These crystallization methods may be employed in combination. The above-mentioned concentration crystallization may be a crystallization method in which the solution containing the above-mentioned solvent is used for replacing a solution containing a solvent other than the above-mentioned solvent. In crystallization, a seed crystal may be added.

The isolating and purifying method can be carried out at around room temperature and, if necessary, heating or cooling may be performed and, for example, it may be carried out at about 60° C. or lower, preferably −40 to 50° C.

The compound (4) obtained in such amanner maybe subjected further to solid-liquid separation. If the quality of it is lowered because of the mother solution remaining in the obtained crystal, the obtained crystal may further be washed and dried, if necessary. The solid-liquid separation method is not particularly limited and, for example, pressure filtration, vacuum filtration, centrifugationor the like method canbe used. Drying may be carried out preferably by reduced pressure drying (vacuum drying) at about 60° C. or lower so as to avoid thermal decomposition or melting.

<Step From the Compound (4) to the Compound (2)>

In this step, the (S)-N-[4-(trifluoromethyl)phenyl]-3-sulfonyloxypentanoic acid amide derivative defined by said formula (4) is cyclized to obtain the (R)-4-ethyl-1-[4-(trifluoromethyl)phenyl]-2-azetidinone defined by said formula (2). $R^1$ is as described above. The cyclization reaction can be carried out by reacting the compound (4) with a base.

The base may include, for example, organolithium reagents such as n-butyl lithium; Grignard reagents such as n-butylmagnesium chloride and tert-butylmagnesium chloride; alkali metal hydrides such as lithium hydride, sodium hydride, and potassium hydride; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and. lithium tert-butoxide; halomagnesium alkoxides such as chloromagnesium methoxide, chloromagnesium tert-butoxide and bromomagnesium tert-butoxide; alkali metal hydroxides such as sodium hydroxide and potassium hydroxide; alkali metal carbonates such as sodium carbonate, potassium carbonate and cesium carbonate; tertiary amines such as triethylamine, 1,7-diazabicyclo-[5,4,0]-undec-7-ene (DBU); etc. Preferable bases are alkali metal hydrides such as sodium hydride and potassium hydride; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide; halomagnesium alkoxides such as chloromagnesium methoxide, chloromagnesium tert-butoxide and bromomagnesium tert-butoxide; alkali metal hydroxides such as sodium hydroxide and potassium hydroxide, and furthermore preferable bases are sodium hydride, sodium methoxide, sodium ethoxide, sodium isopropoxide, sodium tert-butoxide, potassium tert-butoxide, lithium tert-butoxide, sodium hydroxide and potassium hydroxide. The amount of the above-mentioned base to be used is 1 to 10 times, more preferably 1 to 3 times, by mole to that of the above-mentioned compound (4).

The reaction solvent may include, for example, water, alcohol solvents such as methanol, ethanol and isopropanol; ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphonic acid triamide solvents such as hexamethyl phosphonic acid triamide; and the like. Preferred are tetrahydrofuran, ethyl acetate, toluene, methylene chloride, N,N-dimethylformamide, etc. They may be used alone or two or more of them may be used in combination. In the case of using two or more of them in combination, the mixing ratio is not particularly limited. The amount of the above-mentioned reaction solvent to be used is not more than 50 times, preferably 5 to 20 times, by weight to that of the compound (4).

The reaction temperature is preferably −50 to 100° C., more preferably 0 to 50° C. in terms of shortening the reaction time and improving the yield.

The addition method and addition order of the (S)-N-[4-(trifluoromethyl)phenyl]-3-sulfonyloxypentanoic acid amide derivative defined by said formula (4), the base, and the solvent are not particularly limited.

General treatment for obtaining a product from a reaction solution maybe carried out as the treatment after the reaction. For example, water and, optionally, an aqueous acidic solution such as hydrochloric acid or sulfuric acid may be added to the reaction solution for neutralization on completion of the reaction, and then extraction may be carried out using a general extraction solvent, e.g. ethyl acetate, diethyl ether, methylene chloride, toluene, hexane, etc. The aimed substance can be obtained from the extracted solution by removing the reaction solvent and the extraction solvent by heating under vacuum or the like treatment. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography,-etc.

<Step of Isolating and Purifying the Compound (2)>

In this step, a contaminating (S)-4-ethyl-1-[4-(trifluoromethyl)phenyl]-2-azetidinone is removed by crystallization from a hydrocarbon solvent to obtain the (R)-4-ethyl-1-[4-(trifluoromethyl)phenyl]-2-azetidinone defined by said formula (2) as a crystal with improved optical purity.

The above-mentioned hydrocarbon solvent may include, for example, aliphatic hydrocarbon solvents such as pentane, hexane, heptane, cyclohexane, methylcyclohexane, octane and isooctane and aromatic hydrocarbon solvents such as benzene, toluene, o-xylene, m-xylene, p-xylene, 1,3,5-mesitylene and cumene. Aliphatic hydrocarbon solvents such as pentane, hexane, heptane, cyclohexane, methylcyclohexane, octane and isooctane are preferred, and hexane, heptane and methylcyclohexane are more preferred. They may be used alone or two or more of them may be used in combination. In the case of using two or more species, the mixing ratio is not particularly limited.

The amount of the above-mentioned hydrocarbon solvent to be used is preferably sufficient so as to keep the fluidity of the obtained product on completion of the crystallization of the above-mentioned compound (2) and it is preferably, for example, not more than about 50 times, more preferably about 1 to 30 times, by weight to that of the compound (2).

In this step, at the time of crystallization of the above-mentioned compound (2), crystallization methods such as cooling crystallization and concentration crystallization may be employed. These crystallization methods may be employed in combination. The above-mentioned concentration crystallization may be a crystallization method in which the solution containing the above-mentioned solvent is used for replacing a solution containing a solvent other than the above-mentioned solvent. In crystallization, a seed crystal may be added.

The isolating and purifying method can be carried out at around room temperature and, if necessary, heating or cooling may be performed. For example, it may be carried out at about 60° C. or lower, preferably −40 to 50° C.

The above-mentioned compound (2) obtained in such a manner may be subjected further to solid-liquid separation. If the quality of the compound is lowered because of the mother solution remaining in the obtained crystal, the obtained crystal may further be washed and dried, if necessary. The solid-liquid separation method is not particularly limited and, for example, pressure filtration, vacuum filtration, centrifugation or the like method can be used. Drying may be carried out preferably by reduced pressure drying (vacuum drying) at about 60° C. or lower so as to avoid thermal decomposition or melting.

<Step From the Compound (2) to a Compound (5)>

In this step, the (R)-4-ethyl-1-[4-(trifluoromethyl)phenyl]-2-azetidinone defined by said formula (2) is hydrolyzed or alcoholyzed to obtain an (R)-3-[4-(trifluoromethyl)phenylamino]-pentanoic acid derivative defined by the following formula (5):

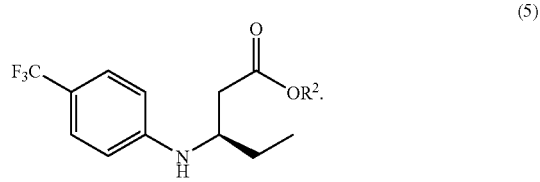

(5)

Here, $R^2$ denotes hydrogen atom or a $C_{1-5}$ alkyl group. The $C_{1-5}$ alkyl group may practically include methyl, ethyl, n-propyl, isopropyl, n-butyl, sec-butyl, tert-butyl, n-pentyl group and the like. $R^2$ is preferably hydrogen atom, or methyl or ethyl group.

In the case of hydrolysis in this step, the process can be carried out by treating the above-mentioned compound (2) with an aqueous acid or an aqueous alkaline solution. The above-mentioned acid may include hydrochloric acid, sulfuric acid, hydrobromic acid, nitric acid, methanesulfonic acid, p-toluenesulfonic acid and the like. Hydrochloric acid and sulfuric acid are preferable. The amount of the above-mentioned acid to be used is preferably 0.1 to 50 times, more preferably 1 to 10 times, by mole to that of the compound (2). The above-mentioned alkali may include, for example, metal hydroxides such as sodium hydroxide, potassium hydroxide, lithium hydroxide, barium hydroxide and the like, and sodium hydroxide and potassium hydroxide are preferable. The amount of the above-mentioned alkali to be used is preferably 1 to 50 times, more preferably 1 to 10 times, by mole to that of the compound (2). The amount of water to be used is preferably 1 to 100 times, more preferably 5 to 20 times, by weight to that of the compound (2).

In the case of alcoholysis in this step, the compound may be treated with an acid or a base in an alcohol solvent to carry out alcoholysis. The alcohol solvent may include, for example, methanol, ethanol, n-propanol, isopropanol, n-butanol, and the like, and methanol and ethanol are preferable. The above alcohol solvent may be used alone or two or more of them may be used in combination. In the case of using two or more of them, the mixing ratio is not particularly limited. The amount of the above-mentioned alcohol solvent to be used is preferably 1 to 100 times, more preferably 5 to 20 times, by weight to that of the compound (2).

The above-mentioned acid may include, for example, hydrogen chloride, sulfuric acid, hydrogen bromide, methanesulfonic acid, p-toluene sulfonic acid and the like, and hydrogen chloride, sulfuric acid and methanesulfonic acid are preferable. The amount of the above-mentioned acid to be used is preferably 0.1 to 50 times, more preferably 1 to 10 times, by mole to that of the compound (2). The above-mentioned base may include, for example, alkali metal hydroxides and alkaline earth metal hydroxides such as sodium hydroxide, potassium hydroxide, lithium hydroxide and barium hydroxide and alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide, and the like. Sodium methoxide and sodium ethoxide are preferable. The amount of the above-mentioned base to be used is preferably 1 to 50 times, more preferably 1 to 10 times, by mole to that of the compound (2).

The reaction temperature is preferably −20 to 100° C., more preferably 0 to 50° C. in terms of shortening the reaction time and improving the yield.

The addition method and addition order of the (R)-4-ethyl-1-[4-(trifluoromethyl)phenyl]-2-azetidinone defined by said formula (2), water or an alcohol, and an acid or a base are not particularly limited.

General treatment for obtaining a product from a reaction solution may be carried out as the treatment after the reaction. For example, water and, optionally, an aqueous alkaline solution such as an aqueous sodium hydroxide solution or an aqueous sodium hydrogen carbonate solution or an aqueous acidic solution such as hydrochloric acid or sulfuric acid may be added to the reaction solution for neutralization on completion of the reaction, and then extraction may be carried out using a general extraction solvent, e.g. ethyl acetate, diethyl ether, methylene chloride, toluene, hexane, etc. The aimed substance can be obtained from the extracted solution by removing the reaction solvent and the extraction solvent by heating under vacuum or the like treatment. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

<Step From the Compound (5) to a Compound (3)>

In this step, the (R)-3-[4-(trifluoromethyl)phenylamino]-pentanoic acid derivative defined by said formula (5) is amidated to obtain (R)-3-[4-(trifluoromethyl)phenylamino]-pentanoic acid amide defined by the following formula (3):

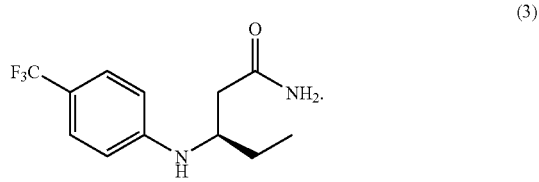

(3)

In the compound (5), $R^2$ is the same as described above.

This step may be carried out with no solvent or using a solvent. In the case of using a solvent, for example, water or an alcohol such as methanol, ethanol, n-propanol, isopropanol, n-butanol, etc. can be used. The above solvent maybe used alone or two or more of themmaybe used in combination. In the case of using two or more species in combination, the mixing ratio is not particularly limited. The amount of water, an alcohol or a mixed solvent of water and an alcohol to be used is preferably not more than 100 times, more preferably not more than 50 times, by weight to that of the compound (5).

The amidation of the step may be carried out by treatment with ammonia.

Here, liquid ammonia or ammonia dissolved in water, an alcohol, e.g. methanol, ethanol, n-propanol, isopropanol, n-butanol, etc., or a mixture thereof may be used. In the case of using the mixture, the mixing ratio is not particularly limited. Ammonia dissolved in water, methanol or ethanol and ammonia dissolved in the mixture of water and methanol or water and ethanol are preferable.

The amount of ammonia to be used is preferably 1 to 100 times, more preferably 10 to 50 times, by mole to that of the compound (5).

The reaction temperature is preferably −20 to 100° C., more preferably 0 to 50° C. in terms of shortening the reaction time and improving the yield.

In this reaction, in the case of using ammonia dissolved in water or in a mixture of water and an alcohol, in order to suppress the competing hydrolysis reaction to the minimum, it is effective to add an ammonium salt. The ammonium salt may include, for example, ammonium chloride, ammonium bromide, ammonium sulfate, ammonium nitrate, ammonium phosphate, ammonium acetate, ammonium formate, ammonium methanesulfonate, ammonium p-toluenesulfonate and the like. Ammonium chloride, ammonium bromide, ammonium sulfate, ammonium acetate and ammonium methanesulfonate are preferable and ammonium chloride is more preferable. These ammonium salts may be prepared in the reaction system by adding an acid to a solvent in which ammonia is dissolved. The above-mentioned acid may include, for example, hydrochloric acid, hydrobromic acid, sulfuric acid, nitric acid, phosphoric acid, acetic acid, formic acid, methanesulfonic acid, p-toluenesulfonic acid and the like. Hydrochloric acid, hydrobromic acid, sulfuric acid, acetic acid and methanesulfonic acid are preferable and hydrochloric acid is more preferable. The amount of the above-mentioned ammonium salt to be used is preferably 0.1 to 50 times, more preferably 1 to 20 times, by mole to that of the compound (5).

In the case that $R^2$ of the compound (5) in the step is hydrogen atom, amidation may be carried out by derivatizing carboxylic acid into an active carbonyl compound and then treating the product with ammonia.

Here, the above-mentioned active carbonyl compound may include, for example, acid chlorides produced by a reaction with a halogenation agent such as thionyl chloride, phosphorus trichloride or oxalyl chloride; mixed acid anhydrides produced by a reaction with a chlorocarbonic acid ester such as methyl chlorocarbonate, ethyl chlorocarbonate or isopropyl chlorocarbonate; mixed acid anhydrides produced by a reaction with a sulfonylation agent such as methanesulfonyl chloride or 4-methylbenzenesulfonyl chloride; acylimidazoles produced by a reaction with carbonyldiimidazole or the like; etc. Acid chlorides produced by a reaction with a halogenation agent such as thionyl chloride, phosphorus trichloride or oxalyl chloride are preferable.

Here, a method for producing an acid chloride by a reaction of the carboxylic acid, which is the compound (5) in which $R^2$ is hydrogen atom, with a halogenation agent such as thionyl chloride, phosphorus trichloride or oxalyl chloride will be described.

The amount of the above-mentioned halogenation agent to be used is preferably 1 to 10 times, more preferably 1 to 3 times, by mole to that of the above-mentioned carboxylic acid.

This step may be carried out without a solvent or using a solvent. In the case of using a solvent, the solvent may include, for example, ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphonic acid triamide solvents such as hexamethyl phosphonic acid triamide; and the like. Preferred are tetrahydrofuran, ethyl acetate, toluene, methylene chloride, N,N-dimethylformamide and the like. They maybe used alone or two or more of themmaybe used in combination. In the case of using two or more of them in combination, the mixing ratio is not particularly limited. The amount of the above-mentioned reaction solvent to be used is preferably not more than 50 times, more preferably 5 to 20 times, by weight to that of the compound (5).

The reaction temperature is preferably −50 to 100° C., more preferably 0 to 50° C. in terms of shortening the reaction time and improving the yield.

As the treatment after the reaction, the reaction solvent is removed by, for example, subjecting the reaction solution to heating under vacuum or the like treatment on completion of the reaction to obtain an aimed substance.

Next, the amidation method by treating the above-mentioned acid chloride with ammonia will be described.

This step may be carried out without a solvent or using a solvent. In the case of using a solvent, the solvent may include, for example, water; alcohol solvents such as methanol, ethanol, n-propanol, isopropanol and n-butanol; ether solvents such as tetrahydrofuran, 1,4-dioxane and ethylene glycol dimethyl ether; and the like. Water and tetrahydrofuran are preferable. These solvents may be used alone or two or more of them may be used in combination. In the case of using two or more of them in combination, the mixing ratio is not particularly limited. The amount of the solvent to be used is preferably not more than 100 times, more preferably not more than 50 times, by weight to that of the above-mentioned acid chloride.

Here, liquid ammonia or ammonia dissolved in water, an alcohol, e.g. methanol, ethanol, n-propanol, isopropanol, n-butanol, etc., or a mixture thereof may be used. In the case of using the mixture, the mixing ratio is not particularly limited. Ammonia dissolved in water, methanol or ethanol and ammonia dissolved in the mixture of water and methanol or water andethanol are preferable. Ammonia dissolvedin water is more preferable.

The amount of ammonia to be used is preferably 1 to 100 times, more preferably 10 to 50 times, by mole to that of the compound (5). The amount of the solvent to be used for dissolving ammonia therein is preferably 1 to 100 times, more preferably 5 to 20 times, by weight to that of the compound (5).

The reaction temperature is preferably −20 to 100° C., more preferably 0 to 50° C. in terms of shortening the reaction time and improving the yield.

The addition method and addition order of the (R)-3-[4-(trifluoromethyl)phenylamino]-pentanoic acid derivative defined by said formula (5) and the reagent and solvent to be used for amidation are not particularly limited.

As the treatment after the reaction, a general treatment for obtaining a product from a reaction solution may be used. For example, heating under vacuum or the like treatment of the reaction solution on completion of the reaction may be carried out to remove the reaction solvent and obtain an aimed product. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

<Step From the Compound (2) to the Compound (3)>

In this step, the (R)-4-ethyl-1-[4-(trifluoromethyl)phenyl]-2-azetidinone defined by said formula (2) is amidated to obtain the (R)-3-[4-(trifluoromethyl)phenylamino]-pentanoic acid amide defined by said formula (3).

This step may be carried out without a solvent or using a solvent. In the case of using a solvent, the solvent may include, for example, water and alcohol solvents such as methanol, ethanol, n-propanol, isopropanol and n-butanol. These solvents may be used alone or two or more of them may be used in combination. In the case of using two or more of them in combination, the mixing ratio is not particularly limited. The amount of water, an alcohol or a mixed solvent of water and an alcohol to be used is preferably not more than 100 times, more preferably not more than 50 times, by weight to that of the compound (2).

Amidation in this step can be carried out by a treatment with ammonia.

Here, liquid ammonia or ammonia dissolved in water, an alcohol, e.g. methanol, ethanol, n-propanol, isopropanol, n-butanol, etc., or a mixture thereof may be used. In the case of using the mixture, the mixing ratio is not particularly limited. Ammonia dissolved in water, methanol or ethanol and ammonia dissolved in the mixture of water and methanol or water and ethanol are preferable.

Incidentally, the reaction also includes the case that the (R)-3-[4-(trifluoromethyl)phenylamino]-pentanoic acid derivative defined by said formula (5) is once produced and is further amidated without being isolated.

The amount of ammonia to be used is preferably 1 to 100 times, more preferably 10 to 50 times, by mole to that of the compound (2).

The reaction temperature is preferably −20 to 100° C., more preferably 0 to 70° C. in terms of shortening the reaction time and improving the yield.

In this reaction, in the case of using ammonia dissolved in water or in a mixture of water and an alcohol, in order to suppress the competing hydrolysis reaction to the minimum, it is effective to add an ammonium salt. The ammonium salt may include, for example, ammonium chloride, ammonium bromide, ammonium sulfate, ammonium nitrate, ammonium phosphate, ammonium acetate, ammonium formate, ammonium methanesulfonate, ammonium p-toluenesulfonate and the like. Ammonium chloride, ammonium bromide, ammonium sulfate, ammonium acetate and ammonium methanesulfonate are preferable and ammonium chloride is more preferable. These ammonium salts may be prepared in the reaction system by adding an acid to a solvent in which ammonia is dissolved. The above-mentioned acid may include, for example, hydrochloric acid, hydrobromic acid, sulfuric acid, nitric acid, phosphoric acid, acetic acid, formic acid, methanesulfonic acid, p-toluenesulfonic acid and the like. Hydrochloric acid, hydrobromic acid, sulfuric acid, acetic acid and methanesulfonic acid are preferable and hydrochloric acid is more preferable. The amount of the above-mentioned ammonium salt to be used is preferably 0.1 to 50 times, more preferably 1 to 20 times, by mole to that of the compound (2).

The addition method and addition order of the (R)-4-ethyl-1-[4-(trifluoromethyl)phenyl]-2-azetidinone defined by said formula (2) and the reagent and solvent to be used for amidation are not particularly limited.

As the treatment after the reaction, a general treatment for obtaining a product from a reaction solution may be used. For example, heating under vacuum or the like treatment of the reaction solution on completion of the reaction may be carried out to remove the reaction solvent and obtain an aimed product. The aimed product obtained in such a manner has a suf ficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

<Step From the Compound (3) to a Compound (8)>

In this step, the (R)-3-[4-(trifluoromethyl)phenylamino]-pentanoic acid amide defined by said formula (3) is reacted with a chlorocarbonic acid ester defined by the following formula (10):

ClCOOR⁴ (10):

in the presence of a base to produce an (R)-3-[4-(trifluoromethyl)phenylamino]-pentanoic acid amide derivative defined by the following formula (8):

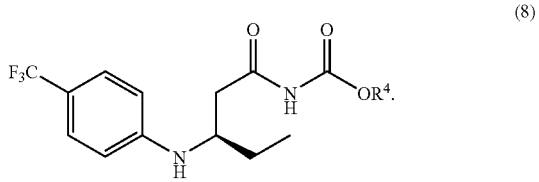

(8)

Here, R⁴ denotes a $C_{1-12}$ alkyl group, a $C_{6-12}$ aryl group or a $C_{7-12}$ aralkyl group. Practically, for example, methyl, ethyl, n-propyl, isopropyl, tert-butyl, phenyl, benzyl, 1-phenylethyl group, etc. can be mentioned. R⁴ is preferably methyl, ethyl, tert-butyl or benzyl group and more preferably methyl or benzyl group.

The amount of the chlorocarbonic acid ester defined by said formula (10) to be used is preferably 1 to 20 times, more preferably 1 to 5 times, by mole to that of the above-mentioned compound (3).

The above-mentioned base may include, for example, organolithium reagents such as n-butyl lithium; Grignard reagents such as n-butylmagnesium chloride and tert-butylmagnesium chloride; alkali metal hydrides such as lithium hydride, sodium hydride and potassium hydride; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide; halomagnesium alkoxides such as chloromagnesium methoxide, chloromagnesium tert-butoxide and bromomagnesium tert-butoxide; alkali metal hydroxides such as sodium hydroxide and potassium hydroxide; alkali metal carbonates such as sodium carbonate, potassium carbonate and cesium carbonate; tertiary amines such as triethylamine, 1,7-diazabicyclo-[5,4,0]-undec-7-ene (DBU); and the like. Preferable are alkali metal hydrides such as sodium hydride and potassium hydride; alkali metal alkoxides such as sodiummethoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide; halomagnesium alkoxides such as chloromagnesium methoxide, chloromagnesium tert-butoxide, bromomagnesium tert-butoxide. More preferable are sodium hydride, sodium methoxide, sodium ethoxide, sodium isopropoxide, sodium tert-butoxide, potassium tert-butoxide and lithium tert-butoxide. The amount of the above-mentioned base to be used is 1 to 10 times, more preferably 1 to 3 times, by mole to that of the above-mentioned compound (3).

The reaction solvent may include, for example, ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphoric acid triamide solvents such as hexamethyl phosphonic acid triamide; and the like. Tetrahydrofuran, ethyl acetate, toluene, methylene chloride, N,N-dimethylformamide and the like are preferred. They may be used alone or two or more of them may be used in combination. In the case of using two or more of them in combination, the mixing ratio is not particularly limited. The amount of the above-mentioned reaction solvent to be used is preferably not more than 50 times, more preferably 5 to 20 times, by weight to that of the above-mentioned compound (3).

The reaction temperature is preferably −50 to 100° C., more preferably −30 to 40° C. in terms of shortening the reaction time and improving the yield.

The addition method and addition order of the (R)-3-[4-(trifluoromethyl)phenylamino]-pentanoic acid amide defined by said formula (3), a chlorocarbonic acid ester, the reagent and the solvent are not particularly limited.

General treatment for obtaining a product from a reaction solution may be carried out as the treatment after the reaction. For example, water and, optionally, an aqueous acidic solution such as hydrochloric acid or sulfuric acid may be added to the reaction solution for neutralization on completion of the reaction, and then extraction may be carried out using a general extraction solvent, e.g. ethyl acetate, diethyl ether, methylene chloride, toluene, hexane, etc. The aimed substance can be obtained from the extracted solution by removing the reaction solvent and the extraction solvent by heating under vacuum or the like treatment. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

<Step From the Compound (2) to the Compound (8)>

In this step, the (R)-4-ethyl-1-[4-(trifluoromethyl)phenyl]-2-azetidinone defined by said formula (2) is reacted with a carbamic acid ester defined by the following formula (9):

$NH_2COOR^4$             (9):

in the presence of a base to produce the (R)-3-[4-(trifluoromethyl)phenylamino]-pentanoic acid amide derivative defined by said formula (8). Here, R⁴ denotes the same as described above.

The amount of the carbamic acid ester defined by said formula (9) to be used is preferably 1 to 20 times, more preferably 1 to 5 times, by mole to that of the above-mentioned compound (2).

The above-mentioned base may include, for example, organolithium reagents such as n-butyl lithium; Grignard reagents such as n-butylmagnesium chloride and tert-butylmagnesium chloride; alkali metal hydrides such as lithium hydride, sodium hydride and potassium hydride; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide; halomagnesium alkoxides such as chloromagnesium methoxide, chloromagnesium tert-butoxide and bromomagnesium tert-butoxide; alkali metal hydroxides such as sodium hydroxide and potassium hydroxide; alkali metal carbonates such as sodium carbonate, potassium carbonate and cesium carbonate; tertiary amines such as triethylamine, 1,7-diazabicyclo-[5,4,0]-undec-7-ene (DBU); and the like. Preferable are alkali metal hydrides such as sodium hydride and potassium hydride; alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium ethoxide, lithium isopropoxide and lithium tert-butoxide; halomagnesium alkoxides such as chloromagnesium methoxide, chloromagnesium tert-butoxide, bromomagnesium tert-butoxide. More preferable are sodium hydride, sodium methoxide, sodium ethoxide, sodium isopropoxide, sodium tert-butoxide, potassium tert-butoxide and lithium tert-butoxide. The amount of the above-mentioned base to be used is 1 to 10 times, more preferably 1 to 3 times, by mole to that of the above-mentioned compound (2).

The reaction solvent may include, for example, ether solvents such as tetrahydrofuran, 1,4-dioxane and ethylene glycol dimethyl ether; ester solvents such as ethyl acetate and isopropyl acetate; hydrocarbon solvents such as benzene, toluene and hexane; ketone solvents such as acetone and methyl ethyl ketone; nitrile solvents such as acetonitrile and propionitrile; halogen solvents such as methylene chloride and chloroform; amide solvents such as N,N-dimethylformamide and N,N-dimethylacetamide; sulfoxide solvents such as dimethyl sulfoxide; urea solvents such as dimethylpropylene urea; phosphonic acid triamide solvents such as hexamethyl phosphonic acid triamide; and the like. Tetrahydrofuran, ethyl acetate, toluene, methylene chloride, N,N-dimethylformamide and the like are preferred. They may be used alone or two or more of them may be used in combination. In the case of using two or more of them in combination, the mixing ratio is not particularly limited. The amount of the above-mentioned reaction solvent to be used is preferably not more than 50 times, more preferably 5 to 20 times, by weight to that of the above-mentioned compound (2).

The reaction temperature is preferably -50 to 100° C., more preferably 0 to 50° C. in terms of shortening the reaction time and improving the yield.

The addition method and addition order of the (R)-4-ethyl-1-[4-(trifluoromethyl)phenyl]-2-azetidinone defined by said formula (2), a carbamic acid ester, the base and the solvent are not particularly limited.

General treatment for obtaining a product from a reaction solution may be carried out as the treatment after the reaction. For example, an aqueous acidic solution such as hydrochloric acid or sulfuric acid may be added to the reaction solution for neutralization on completion of the reaction, and then extraction maybe carried out using a general extraction solvent, e.g. ethyl acetate, diethyl ether, methylene chloride, toluene, hexane, etc. The aimed substance can be obtained from the extracted solution by removing the reaction solvent and the extraction solvent by heating under vacuum or the like treatment. The aimed product obtained in such a manner has a sufficient purity to be subjected to the successive steps. Furthermore, for the purpose of further improvement of the yield in the successive steps or the purity of the compound to be obtained in the successive steps, the purity of the product may further be improved by a general purifying technique such as crystallization, fractional distillation, column chromatography, etc.

The invention provides a production method for easily and economically producing an (R)-3-[4-(trifluoromethyl)phenylamino]-pentanoic acid amide derivative useful for an intermediate for pharmaceutical product, more particularly as an inhibitor of a cholesteryl ester transfer protein (CETP), from easily available raw materials.

BEST MODE FOR CARRYING OUT THE INVENTION

The invention will be described more particularly with reference to Examples as follows, however it is not intended to limit the scope of the invention to the illustrated Examples.

Additionally, in Examples, the isolated yield is a yield calculated by assuming that the purity of the product obtained by isolating and purifying process through silica gel chromatography or the like is 100 wt %. The crude yield is a yield calculated by assuming that the purity of the un-purified product is 100 wt %. The recovery ratio is a percentage of the product weight obtained after crystallization to that before crystallization.

EXAMPLE 1

Production of N-[4-(trifluoromethyl)phenyl]-3-oxopentanoic acid amide

Methyl 3-oxopentanoate 10.0 g (76.8 mmol) was heated to 115° C. and 4-(trifluoromethyl)aniline 12.83 g (79.6 mmol) was added dropwise thereto for 10 minutes. After stirring at the same temperature for 25 minutes, toluene (50 mL) was added and the resulting reaction solution was further heated and stirred for 12 hours. The reaction solution was cooled to 0° C. to precipitate a solid and subjected to vacuum filtration to obtain N-[4-(trifluoromethyl)phenyl]-3-oxopentanoic acid amide as a white solid (11.22 g, isolated yield: 57%). $^1$H-NMR (CDCl$_3$, 400 MHz/ppm): δ 1.13 (3H, t), 2.64 (2H, q), 3.60 (2H, s), 7.58 (2H, d), 7.69 (2H, d), 9.52 (1H, br)

EXAMPLE 2

Production of (S)-N-[4-(trifluoromethyl)phenyl]-3-hydroxypentanoic acid amide

N-[4-(trifluoromethyl)phenyl]-3-oxopentanoic acid amide 1.30 g (5.0 mmol) produced in Example 1 and ((S)-BINAP)RuBr$_2$ 50.0 mg (0.057 mmol) (BINAP denotes 2,2'-bisdiphenylphosphino-1,1'-binaphthyl. It was prepared according to the method described in Tetrahedron Asymmetry, 1994,5,675) were mixed with 20 mL of a methanol-water (10/1 in volume) solution. Hydrogen replacement was carried out three times and after the reaction solution was heated to 60° C., reaction was carried out under hydrogen pressure (3.0 kg/cm$^2$) for 12 hours. After releasing hydrogen, the solution was concentrated under reduced pressure and purifying on silica gel chromatography was carried out to obtain (S)-N-[4-(trifluoromethyl)phenyl]-3-hydroxypentanoic acid amide as a white solid (1.23 g, isolated yield: 95%). The optical purity of the product was determined by HPLC analysis (column; Daicel Chiral Pack AD-H 4.6×250 mm: eluent; hexane/isopropanol=90/10: flow rate; 1.0 mL/min: column temperature; 30° C.: detector; UV 210 nm: retention time; (S) antipode=12.0 minutes, (R) antipode=9.3 minutes) to be 84.7% ee. $^1$H-NMR (CDCl$_3$, 400 MHz/ppm): δ 1.00 (3H, t), 1.5-1.7 (2H, br), 2.50 (1H, dd), 2.59 (1H, dd), 2.75 (br, 1H), 4.06 (1H, m), 7.57 (2H, d), 7.64 (2H, d), 8.21 (1H, br)

EXAMPLE 3

Production of (S)-N-[4-(trifluoromethyl)phenyl]-3-methanesulfonyloxypentanoic acid amide A tetrahydrofuran solution (2 mL) containing 703 mg (6.14 mmol) of methanesulfonyl chloride was added dropwise to a tetrahydrofuran solution (8 mL) containing 1.07 g (4.09 mmol) of (S)-N-[4-(trifluoromethyl)phenyl]-3-hydroxypentanoic acid amide produced in Example 2 and 621 mg (6.14 mmol) of triethylamine at 0° C. for 10 minutes. After stirring at the same temperature for 1hour, water (25 mL) and ethyl acetate (30 mL) were added to carry out extraction. The organic layer was washed with saturated brine, and dried with anhydrous sodium sulfate. The solvent was removed by distillation under reduced pressure to obtain (S)-N-[4-(trifluoromethyl)phenyl]-3-methanesulfonyloxypentanoic acid amide as a yellow solid (1.48 g, crude yield: 97%). $^1$H-NMR (CDCl$_3$, 400 MHz/ppm): δ 1.04 (3H, t), 1.91 (2H, m), 2.73-2.87 (2H, m), 3.15 (3H, s), 5.01-5.09 (1H, m), 7.56 (2H, d), 7.66 (2H, d), 7.83 (1H, br)

EXAMPLE 4

Production of (S)-N-[4-(trifluoromethyl)phenyl]-3-(4-methylphenyl)sulfonyloxypentanoic acid amide To a solution containing 300 mg (1.15 mmol) of (S)-N-[4-(trifluoromethyl)phenyl]-3-hydroxypentanoic acid amide produced in Example 2 and pyridine (0.9 mL), 328.4 mg (1.72 mmol) of 4-methylbenzenesulfonyl chloride was added at 0° C. After stirring at 0° C. for 5 hours and at room temperature for further 5 hours, water (5 mL) was added and the resultant was stirred at room temperature for 2 hours. Extraction was carried out with ethyl acetate and after the organic layer was washed with saturated brine, the product was dried with anhydrous sodium sulfate. The solvent was removed by distillation under reduced pressure and purifying was carried out on silica gel column chromatography to obtain (S)-N-[4-(trifluoromethyl)phenyl]-3-(4-methylphenyl)sulfonyloxypentanoic acid amide as a white solid (455.1 mg, isolated yield: 49%). $^1$H-NMR (CDCl$_3$, 400 MHz/ppm): δ 0.86 (3H, t), 1.75-1.82 (2H, m), 2.38 (3H, s), 2.72-2.83 (2H, m), 4.87-4.93 (1H, m), 7.23-7.26 (2H, m), 7.54-7.59 (4H, m), 7.74-7.78 (3H, m)

EXAMPLE 5

Production of (R)-4-ethyl-1-[4-(trifluoromethyl)phenyl]-2-azetidinone 158.7 mg of sodium hydride (60 wt %; 3.97 mmol) was suspended in a mixed solution of dichloromethane (2.7 mL) and dimethylformamide (10.8 mL) and to the solution, a mixed solution of 1,346.2 mg (3.97 mmol) of (S)-N-[4-(trifluoromethyl)phenyl]-3-methanesulfonyloxypentanoic acid amide produced in Example 3, dichloromethane (2.7 mL) and dimethylformamide (10.8 mL) was added dropwise at room temperature for 15 minutes. After stirring at room temperature for further 1 hour, water (25 mL) was added and extraction was carried out with ethyl acetate. The organic layer was washed with saturated brine and the product was dried with anhydrous sodium sulfate. The solvent was removed by distillation under reduced pressure to obtain (R)-4-ethyl-1-[4-(trifluoromethyl)phenyl]-2-azetidinone as a brown solid (996.3 mg, crude yield: 87%). The optical purity of the product was determined by HPLC analysis (column; Daicel Chiral Pack AD-H 4.6×250 mm: eluent; hexane/isopropanol=95/5: flow rate; 1.0 mL/min: column temperature; 30° C.: detector; UV 210 nm: retention time; (S) antipode=7.6 minutes, (R) antipode=8.8 minutes) to be 83.0% ee. $^1$H-NMR (CDCl$_3$, 400 MHz/ppm): δ 0.99 (3H, t), 1.63-1.73 (1H, m), 2.11-2.21 (1H, m), 2.79 (1H, dd), 3.23 (1H, dd), 4.07-4.13 (1H, m), 7.47 (2H, d), 7.58 (2H, d)

EXAMPLE 6

Isolation and Purification of (R)-4-ethyl-1-[4-(trifluoromethyl)phenyl]-2-azetidinone (R)-4-ethyl-1-[4-(trifluoromethyl)phenyl]-2-azetidinone produced in Example 5 was purified on silica gel column chromatography to obtain a yellow solid (864 mg). The obtained solid was suspended in hexane (5.7 mL), dissolved by heating to 50° C., then gradually cooled to 0° C. and stirred at the same temperature for 1 hour. The precipitated crystal was filtered under reduced pressure to obtain (R)-4-ethyl-1-[4-(trifluoromethyl)phenyl]-2-azetidinone as a white crystal (454.3 mg, recovery ratio: 47%). The optical purity of the product was determined according to the method described in Example 5 to be 100% ee.

EXAMPLE 7

Production of (R)-4-ethyl-1-[4-(trifluoromethyl)phenyl]-2-azetidinone 31.8 mg (0.589 mmol) of sodium methoxide was suspended in tetrahydrofuran (1 mL) and a tetrahydrofuran solution (1 mL) containing 200 mg (0.589 mmol) of (S)-N-[4-(trifluoromethyl)phenyl]-3-methanesulfonyloxypentanoic acid amide produced in Example 3 was added dropwise thereto at room temperature for 5 minutes. After stirring at room temperature for further 3.5 hours, water (5 mL) was added and extraction was carried out with ethyl acetate. The organic layer was washed with saturated brine and the product was dried with anhydrous sodium sulfate. The solvent was removed by distillation under reduced pressure to obtain (R)-4-ethyl-1-[4-(trifluoromethyl)phenyl]-2-azetidinone as a brown solid (141.6 mg). The reaction yield of the product was determined by HPLC analysis (column; NACALAI COSMO SEAL 5C$_{18}$-AR packed column 4.6×250 mm: eluent; acetonitrile/5 mM phosphate buffer solution (pH=3)=1/1: flow rate; 1.0 mL/min: column temperature; 30° C: detector; UV 210 nm) to be 60%.

EXAMPLE 8

Production of (R)-4-ethyl-1-[4-(trifluoromethyl)phenyl]-2-azetidinone 99.2 mg (0.884 mmol) of potassium tert-butoxide was suspended in tetrahydrofuran (1.5 mL) and a tetrahydrofuran solution (1.5 mL) containing 300 mg (0.884 mmol) of (S)-N-[4-(trifluoromethyl)phenyl]-3-methanesulfonyloxypentanoic acid amide produced in Example 3 was added dropwise thereto at room temperature for 5 minutes. After stirring at room temperature for further 5.5 hours, water (5 mL) was added and extraction was carried out with ethyl acetate. The organic layer was washed with saturated brine and the product was dried with anhydrous sodium sulfate. The solvent was removed by distillation under reduced pressure to obtain (R)-4-ethyl-1-[4-(trifluoromethyl)phenyl]-2-azetidinone as a brown solid (194.0 mg). The reaction yield of the product was determined by the method described in Example 7 to be 81%.

EXAMPLE 9

Production of (R)-4-ethyl-1-[4-(trifluoromethyl)phenyl]-2-azetidinone

To a tetrahydrofuran solution (1 mL) containing 200 mg (0.589 mmol) of (S)-N-[4-(trifluoromethyl)phenyl]-3-methanesulfonyloxypentanoic acid amide produced in Example 3, 368.4 mg (0.589 mmol) of tert-butylmagnesium chloride tetrahydrofuran solution (1.6 mmol/g) was added dropwise at room temperature for 5 minutes. After stirring at room temperature for further 2 hours, water (5 mL) was added and extraction was carried out with ethyl acetate. The organic layer was washed with saturated brine and the product was dried with anhydrous sodium sulfate. The solvent was removed by distillation under reduced pressure to obtain (R)-4-ethyl-1-[4-(trifluoromethyl)phenyl]-2-azetidinone as a brown solid (136.4 mg). The reaction yield of the product was determined by the method described in Example 7 to be 61%.

EXAMPLE 10

Production of (R)-4-ethyl-1-[4-(trifluoromethyl)phenyl]-2-azetidinone 26.5 mg of sodium hydride (60 wt %; 0.662 mmol) was suspended in tetrahydrofuran (1.5 mL) and to the solution, a tetrahydrofuran solution (1.5 mL) containing 274.9 mg (0.662 mmol) of (S)-N-[4-(trifluoromethyl)phenyl]-3-(4-methylphenyl)sulfonyloxypentanoic acid amide produced in Example 4 was added dropwise at room temperature for 5 minutes. After stirring at room temperature for further 3.5 hours, water (5 mL) was added and extraction was carried out with ethyl acetate. The organic layer was washed with saturated brine and the product was dried with anhydrous sodium sulfate. The solvent was removed by distillation under reduced pressure to obtain (R)-4-ethyl-1-[4-(trifluoromethyl)phenyl]-2-azetidinone as a brown solid (176.1 mg). The reaction yield of the product was determined by the method described in Example 7 to be 83%.

EXAMPLE 11

Production of (R)-4-ethyl-1-[4-(trifluoromethyl)phenyl]-2-azetidinone

To a suspension containing 200 mg (0.77 mmol) of (S)-N-[4-(trifluoromethyl)phenyl]-3-hydroxypentanoic acid amide produced in Example 2, triphenylphosphine (1,188 mg, 1.53 mmol), and tetrahydrofuran (1 mL), a tetrahydrofuran solution (1 mL) containing 309.8 mg (1.53 mmol) of diisopropyl azodicarboxylate was added dropwise at room temperature for 5 minutes. After stirring at the same temperature for further 1.5 hours, the solvent was removed by distillation under reduced pressure to obtain an oil. When diethyl ether cooled to 0° C. was added to the oil, a solid was precipitated, which was removed by vacuum filtration. The filtrate was concentrated under reduced pressure to obtain a white solid (342.0 mg). The reaction yield of the product was determined by the method described in Example 7 to be 30%.

EXAMPLE 12

Production of Methyl (R)-3-[4-(trifluoromethyl)phenylamino]-pentanoate 420 mg (1.73 mmol) of (R)-4-ethyl-1-[4-(trifluoromethyl)phenyl]-2-azetidinone produced in Example 6 was dissolved in methanol (7.0 mL) and further mixed with 668 mg (3.46 mmol) of 28 wt % sodium methoxide/methanol solution at room temperature. After stirring at the same temperature for further 1 hour, the solvent was removed by distillation under reduced pressure and 1 N hydrochloric acid (5.0 mL) was added and extraction with ethyl acetate was carried out. The organic layer was washed with an aqueous saturated sodium hydrogen carbonate solution, and the product was dried with anhydrous magnesium sulfate and concentrated under reduced pressure to obtain methyl (R)-3-[4-(trifluoromethyl)phenylamino]-pentanoate as a colorless oil (459 mg, crude yield: 97%).

The optical purity of the product was determined by HPLC analysis (column; Daicel Chiral Pack AD-H 4.6×250 mm: eluent; hexane/isopropanol=95/5: flow rate; 1.0 mL/min: column temperature; 30° C.: detector; UV 210 nm: retention time; (S) antipode=7.0 minutes, (R) antipode=5.9 minutes) to be 100% ee. $^1$H-NMR (CDCl$_3$, 400 MHz/ppm): δ 0.98 (3H, t), 1.63 (2H, dq), 2.55 (2H, dd), 3.66 (3H, s), 3.79 (1H, m), 4.12 (1H, brs), 6.62 (2H, d), 7.38 (2H, d)

EXAMPLE 13

Production of Ethyl (R)-3-[4-(trifluoromethyl)phenylamino]-pentanoate

To 200 mg (0.822 mmol) of (R)-4-ethyl-1-[4-(trifluoromethyl)phenyl]-2-azetidinone produced in Example 6, 2.0 g (16.45 mmol) of 30 wt % hydrogen chloride/ethanol solution was added dropwise for 5 minutes. On completion of the addition, the resulting solution was heated to 40° C. and stirred for 14 hours. Water (5 mL) was added to the solution and extraction with ethyl acetate was carried out. The extracted organic layer was washed with saturated brine and the product was dried with anhydrous sodium sulfate. The solvent was removed by distillation under reduced pressure to obtain ethyl (R)-3-[4-(trifluoromethyl) phenylamino]-pentanoate as a yellow oil (193.8 mg, crude yield: 82%). $^1$H-NMR (CDCl$_3$, 400 MHz/ppm): 6 0.98 (3H, t), 1.23 (3H, t), 1.55-1.71 (2H, m), 2.53 (2H, m), 3.75-3.82 (1H, m), 4.11 (2H, q), 6.61 (2H, d), 7.38 (2H, d)

EXAMPLE 14

Production of (R)-3-[4-(trifluoromethyl)phenylamino]-pentanoic acid amide 403 mg (1.47 mmol) of methyl (R)-3-[4-(trifluoromethyl)phenylamino]-pentanoate produced in Example 12 was dissolved in methanol (20 mL) and further mixed with a 28 wt % aqueous ammonia solution (30 mL) at room temperature. After stirring at the same temperature for further 63 hours, the reaction solution was concentrated under reduced pressure and subjected to extraction with ethyl acetate. The product was then dried with anhydrous magnesium sulfate. The residue obtained by removing the solvent by distillation under reduced pressure was purified on silica gel column chromatography to obtain (R)-3-[4-(trifluoromethyl)phenylamino]-pentanoic acid amide as a white solid (183 mg, isolated yield: 48%). The optical purity of the product was determined by HPLC analysis (column; Daicel Chiral Pack AD-H 4.6×250 mm: eluent; hexane/isopropanol=95/5: flow rate; 1.0 mL/min: column temperature; 30° C.: detector; UV 210 nm: retention time; (S) antipode=23.5 minutes, (R) antipode=24.8 minutes) to be 100% ee. $^1$H-NMR (CDCl$_3$, 400 MHz/ppm): δ 0.98 (3H, t), 1.65 (2H, m), 2.45 (2H, d), 3.76 (1H, m), 4.28 (1H, d), 5.58 (2H, brs), 6.64 (2H, d), 7.38 (2H, d)

EXAMPLE 15

Production of (S)-N-[4-(trifluoromethyl)phenyl]-3-hydroxypentanoic acid amide

A liquid culture medium (pH 7.0) 5 mL containing polypeptone 10 g, meat extract 10 g, and yeast extract 5 g (all per 1 L) was loaded in each test tube and subjected to steam sterilization at 120° C. for 20 minutes. Each one platinum loop amount of microorganism shown in Table 1 was aseptically inoculated into the test tube and cultured at 30° C. for 24 hours with stirring. After the culture, a cell was collected by centrifuging the culture medium and suspended in 100 mM phosphate buffer solution (pH 7.0) 1 mL. To the obtained buffer solution, N-[4-(trifluoromethyl)phenyl]-3-oxopentanoic acid amide 5 mg obtained in Example 1 and glucose 5 g were added and the resultant was stirred at 30° C. for 24 hours. On completion of the reaction, ethyl acetate 5 mL was added for extraction. Accordingto the method described in Example 2, the yield and the optical purity of the produced (S)-N-[4-(trifluoromethyl)phenyl]-3-hydroxypentanoic acid amide were measured and the results are shown in Table 1.

TABLE 1

| Microorganisms | | | Yield (%) | Optical purity (% ee) |
|---|---|---|---|---|
| Arthrobacter | paraffineus | ATCC21218 | 10 | 90.7 |
| Bacillus | subtilis | IAM1193 | 4 | >99 |
| Bacillus | cereus | IFO3466 | 5 | >99 |
| Bacillus | licheniformis | IFO12195 | 8 | 98.6 |
| Bacillus | amyloliquefacieus | IFO3022 | 2 | 97.9 |
| Paenibacillus | amylolyticus | IFO13625 | 9 | 95.7 |
| Paenibacillus | polymyxa | IFO3020 | 9 | >99 |
| Paenibacillus | alvei | IFO3343 | 11 | >99 |
| Brevibacterium | iodinum | IFO3558 | 3 | 92.9 |
| Clostridium | cylindrosporum | IFO13695 | 31 | 96.7 |
| Rathayibacter | rathayi | JCM9307 | 4 | >99 |
| Corynebacterium | xerosis | IFO12684 | 9 | >99 |
| Corynebacterium | flavescens | JCM1317 | 5 | 98.5 |
| Flavobacterium | flavescens | JCM7456 | 35 | 96.2 |
| Luteococcus | japonicus | IFO12422 | 4 | 98.7 |
| Microbacterium | lacticum | JCM1397 | 6 | >99 |
| Nocardia | globerula | IFO13510 | 5 | 99.0 |
| Pseudomonas | stutzeri | IFO13596 | 28 | 97.9 |
| Pseudomonas | fluorescens | IFO3081 | 7 | 97.4 |
| Serratia | marcescens | IFO3046 | 2 | 98.1 |
| Rhodococcus | erythropolis | IFO12320 | 2 | >99 |

EXAMPLE 16

Production of (S)-N-[4-(trifluoromethyl)phenyl]-3-hydroxypentanoic acid amide

A liquid culture medium (pH 7.0) 5 mL containing glucose 40 g, yeast extract 3 g, diammonium hydrogen phosphate 6.5 g, dipotassium hydrogen phosphate 1 g, magnesium sulfate heptahydrate 0.8 g, zinc sulfate heptahydrate 60 mg, iron sulfate heptahydrate 90 mg, copper sulfate pentahydrate 5 mg, manganese sulfate tetrahydrate 10 mg and sodium chloride 100 mg (all per 1 L) was loaded in each test tube and subjected to steam sterilization at 120° C. for 20 minutes. Each one platinum loop amount of microorganism shown in Table 2 was aseptically inoculated into the test tube and cultured at 30° C. for 24 hours with stirring. After the culture, a cell was collected by centrifuging the culture medium and suspended in 100 mM phosphate buffer solution (pH 7.0) 1 mL. To the obtained buffer solution, N-[4-(trifluoromethyl)phenyl]-3-oxopentanoic acid amide 5 mg obtained in Example 1 and glucose 5 g were added and stirred at 30° C. for 24 hours. On completion of the reaction, ethyl acetate 5 mL was added for extraction. According to the method described in Example 2, the yield.and the optical purity of the produced (S)-N-[4-(trifluoromethyl)phenyl]-3-hydroxypentanoic acid amide were measured and the results are shown in Table 2.

TABLE 2

| Microorganisms | | | Yield (%) | Optical purity (% ee) |
|---|---|---|---|---|
| Candida | guilliermondii | IFO 0454 | 21 | 18.6 |
| Candida | intermedia | IFO 0761 | 89 | 96.3 |
| Candida | molischiana | IFO 10296 | 44 | 98.5 |
| Cryptococcus | albidus | IFO 0378 | 12 | 5.4 |

EXAMPLE 17

Production of (R)-3-[4-(trifluoromethyl)phenylamino]-pentanoic acid 2.91 g (12.0 mmol) of (R)-4-ethyl-1-[4-(trifluoromethyl)phenyl]-2-azetidinone produced in Example 6 was dissolved in methanol (15 mL) and further mixed with water (10 mL) and potassium hydroxide (1.34 g, 23.9 mmol). The resulting solution was stirred at room temperature for 14 hours. On completion of the reaction, methanol was removed by distillation and toluene (10 mL) and water (5 mL) were added to separate the solution. The separated organic layer was further mixed with water (15.2 mL) and a 30 wt % aqueous solution of potassiumhydroxide (1.02 g) to separate the solution again. The separated aqueous layers were collected together and adjusted to be pH=1.5 by concentrated hydrochloric acid and extraction with toluene (20 mL) was repeated three times. The residue obtained by concentrating the organic layer was crystallized from toluene (9 mL)/hexane (35 mL) to obtain (R)-3-[4-(trifluoromethyl)phenylamino]-pentanoic acid as awhite crystal (2.38 g, isolated yield: 76%). $^1$H-NMR (CDCl$_3$, 400 MHz/ppm): δ 0.90 (3H, t), 1.5-1.8 (2H, m), 2.4-2.5 (2H, m), 3.7-3.9 (1H, m), 6.65 (2H, d), 7.39 (2H, d)

EXAMPLE 18

Production of (R)-3-[4-(trifluoromethyl)phenylamino]-pentanoic acid amide

To 200 mg (0.76 mmol) of (R)-3-[4-(trifluoromethyl)phenylamino]-pentanoic acid produced in Example 17, 2.0 g (16.8 mmol) of thionyl chloride was added and stirred at room temperature for 1 hour. After being concentrated, the reaction solution was dissolved in tetrahydrofuran (1.5 mL)

and mixed with a 28 wt % aqueous ammonia solution (3.0 g). The obtained solution was stirred at room temperature for 30 minutes and subjected to extraction with ethyl acetate. The residue obtained by concentrating the organic layer dried with magnesium sulfate was crystallized from ethyl acetate (1.0 mL)/hexane (4.0 mL) to obtain (R)-3-[4-(trifluoromethyl)phenylamino]-pentanoic acid amide as a white crystal (141 mg, isolated yield: 71%). The optical purity of the product was determined by the method described in Example 14 to be 99%ee or higher.

EXAMPLE 19

Production of methyl (R)-{3-[4-(trifluoromethyl)phenylamino]-pentanoyl}carbamate 866 mg (3.57 mmol) of (R)-4-ethyl-1-[4-(trifluoromethyl)phenyl]-2-azetidinone produced in Example 6 and 402 mg (5.4 mmol) of methyl carbamate were dissolved in tetrahydrofuran (15 mL) and further mixed with a lithium tert-butoxide/tetrahydrofuran solution (1 mol/L, 5.4 mL, 5.4 mmol) at room temperature. After stirring at the same temperature for 2 hours, water (5.0 mL) was further added to the reaction solution and extraction with toluene (10 mL) was repeated twice. The residue obtained by concentration of the separated organic layer after washing with water was purified on silica gel column chromatography to obtain methyl (R)-{3-[4-(trifluoromethyl)phenylamino]-pentanoyl}carbamate as a white solid (897 mg, isolated yield: 79%). $^1$H-NMR (CDCl$_3$, 400 MHz/ppm): δ 0.98 (3H, t), 1.5-1.8 (2H, m), 2.9-3.2 (2H, m), 3.77 (3H, s), 3.8-3.9 (1H, m), 4.2-4.3 (1H, br), 6.60 (2H, d), 7.37 (2H, d), 7.9-8.1 (1H, br)

EXAMPLE 20

Production of benzyl (R)-{3-[4-(trifluoromethyl)phenylamino]-pentanoyl}carbamate 80.0 mg (0.33 mmol) of (R)-4-ethyl-1-[4-(trifluoromethyl)phenyl]-2-azetidinone produced in Example 6 and 74.8 mg (0.50 mmol) of benzyl carbamate were dissolved in tetrahydrofuran (3 mL) and further mixed with a lithium tert-butoxide/tetrahydrofuran solution (1 mol/L, 0.50 mL, 0.50 mmol) at room temperature. After stirring at the same temperature for 1.5 hours, water (5.0 mL) was further added to the reaction solution and extraction with ethyl acetate (5 mL) was repeated three times. The residue obtained by concentrating the separated organic layer dried with anhydrous magnesium sulfate was purified on silica gel column chromatography to obtain benzyl (R)-{3-[4-(trifluoromethyl)phenylamino]-pentanoyl}carbamate as a white solid (112 mg, isolated yield: 86%). $^1$H-NMR (CDCl$_3$, 400 MHz/ppm): δ 0.98 (3H, t), 1.5-1.8 (2H, m), 2.9-3.2 (2H, m), 3.8-3.9 (1H, m), 4.2-4.3 (1H, br), 5.17 (2H, s), 6.60 (2H, d), 7.3-7.4 (7H, m), 7.5-7.6 (1H, br)

EXAMPLE 21

Production of methyl (R)-{3-[4-(trifluoromethyl)phenylamino]-pentanoyl}carbamate A solution containing 520 mg (2.0 mmol) of (R)-3-[4-(trifluoromethyl)phenylamino]-pentanoic acid amide produced in Example 14, 283.5 mg (3.0 mmol) of methyl chlorocarbonate, and tetrahydrofuran (3 mL) was cooled to −10° C. and to the solution, a lithium tert-butoxide/tetrahydrofuran solution (1 mol/L, 6.0 mL, 6.0 mmol) was added dropwise for 15 minutes. After stirring at the same temperature for 1 hour, water (5.0 mL) was further added to the reaction solution. Extraction with ethyl acetate (20 mL) was carried out, and the obtained organic layer was washed with saturated brine and then dried with anhydrous magnesium sulfate. The solvent was removed by distillation under reduced pressure to obtain 720.6 mg of a brown oil. The obtained product was purified on silica gel column chromatography to obtain methyl (R)-{3-[4-(trifluoromethyl)phenylamino]-pentanoyl}carbamate as a white solid (586 mg, isolated yield: 92%).

EXAMPLE 22

Isolation and Purification of (S)-N-[4-(trifluoromethyl)phenyl]-3-methanesulfonyloxypentanoic acid amide Toluene (8 g) was added to (S)-N-[4-(trifluoromethyl)phenyl]-3-methanesulfonyloxypentanoic acid amide (2.0 g, optical purity: 92.8% ee.) produced in Example 3, and the mixture was heated at 50° C. to be homogeneous. Hexane (4.6 g) was added thereto, and the mixture was stirred for 30 minutes at 50° C. Then, the mixture was cooled to 20° C. and further stirred for 1 hour. The precipitated crystal was filtered under reduced pressure, and subjected to vacuum drying to obtain (S)-N-[4-(trifluoromethyl)phenyl]-3-methanesulfonyloxypentanoic acid amide as a white crystal (1.77 g, recovery ratio: 88%). The optical purity of the product was determined by HPLC analysis (column; Daicel Chiralcel OD-H 4.6×250 mm: eluent; hexane/isopropanol=9/1 (v/v): flow rate; 1.0 mL/min: column temperature; 30° C.: detector; UV 210 nm: retention time; (S) antipode=11.1 minutes, (R) antipode=14.9 minutes) to be 100% ee.

EXAMPLE 23

Isolation and Purification of (S)-N-[4-(trifluoromethyl)phenyl]-3-methanesulfonyloxypentanoic acid amide P-xylene (18 g) was added to (S)-N-[4-(trifluoromethyl)phenyl]-3-methanesulfonyloxypentanoic acid amide (2.0 g, optical purity: 92.8% ee.) produced in Example 3, and the mixture was heated at 50° C. to be homogeneous. Hexane (4.5 g) was added thereto, and the mixture was stirred at 50° C. for 30 minutes. Then, the mixture was cooled to 20° C. and stirred for further 1 hour. The precipitated crystal was filtered under reduced pressure, and subjected to vacuum drying to obtain (S)-N-[4-(trifluoromethyl)phenyl]-3-methanesulfonyloxypentanoic acid amide as a white crystal (1.65 g, recovery ratio: 82%). The optical purity of the product was determined according to the method described in Example 22 to be 100% ee.

What is claimed is:
1. (S)-N-[4-(trifluoromethyl)phenyl]-3-hydroxypentanoic acid amide defined by the following formula (1):

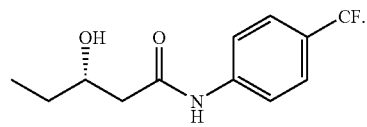

2. (R)-4-ethyl-1-(4-(trifluoromethyl)phenyl]-2-azetidinone defined by the following formula (2):

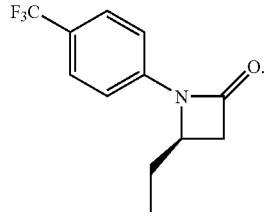

(2)

3. An (S)-N-[4-(trifluoromethyl)phenyl]-3-sulfonyloxypentanoic acid amide derivative defined by the following formula (4):

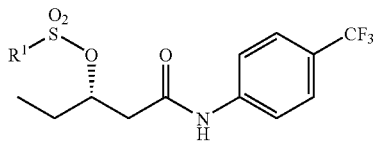

in the formula, $R^1$ denotes a $C_{1-12}$ alkyl group optionally having a substituent or a $C_{6-12}$ aryl group optionally having a substituent.

4. The (S)-N-[4-(trifluoromethyl)phenyl]-3-sulfonyloxypentanoic acid amide derivative according to claim 3, wherein $R^1$ is methyl or 4-methylphenyl group.

* * * * *